US006759246B1

(12) United States Patent
Collins

(10) Patent No.: US 6,759,246 B1
(45) Date of Patent: Jul. 6, 2004

(54) HEMATOLOGY CONTROL COMPOSITION INCLUDING LYMPHOCYTE ANALOGS AND METHOD FOR PREPARATION AND USE

(75) Inventor: Mark Collins, Maple Grove, MN (US)

(73) Assignee: Research & Diagnostic Systems, Inc., Minneapolis, MN (US)

( * ) Notice: Subject to any disclaimer, the term of this patent is extended or adjusted under 35 U.S.C. 154(b) by 132 days.

(21) Appl. No.: 09/997,913

(22) Filed: Nov. 30, 2001

(51) Int. Cl.$^7$ .............................................. G01N 31/00
(52) U.S. Cl. .............................. 436/10; 436/8; 436/16; 436/17; 436/63; 436/174; 422/73; 435/2; 252/408.1
(58) Field of Search ................................ 436/8, 10, 63, 436/17, 18, 16, 174; 422/73; 252/408.1; 435/2

(56) References Cited

U.S. PATENT DOCUMENTS

| | | | |
|---|---|---|---|
| 3,741,875 A | 6/1973 | Ansley et al. ............ 195/103.5 |
| 4,099,917 A | 7/1978 | Kim ............................ 436/10 |
| 4,160,644 A | 7/1979 | Ryan ........................... 436/10 |
| 4,488,564 A * | 12/1984 | Grollier et al. ............. 132/202 |
| 4,704,364 A | 11/1987 | Carver et al. ................. 436/10 |
| 4,876,189 A | 10/1989 | Schetters et al. .............. 435/7 |
| 5,112,871 A | 5/1992 | Austin ........................ 514/727 |
| 5,180,508 A * | 1/1993 | Birkhan et al. ............. 510/522 |
| 5,227,304 A * | 7/1993 | Wong .......................... 436/17 |
| 5,270,208 A | 12/1993 | Ryan ........................... 436/10 |
| 5,320,964 A * | 6/1994 | Young et al. ................. 436/10 |
| 5,380,664 A * | 1/1995 | Carver et al. ................. 436/10 |
| 5,459,073 A | 10/1995 | Ryan ........................... 436/16 |
| 5,460,797 A | 10/1995 | Ryan ......................... 435/40.5 |
| 5,512,485 A | 4/1996 | Young et al. ................. 436/10 |
| 5,529,933 A * | 6/1996 | Young et al. ................. 436/10 |
| 5,677,145 A * | 10/1997 | Ryan ........................... 436/10 |
| 5,858,790 A * | 1/1999 | Kim et al. .................... 436/16 |
| 5,994,139 A * | 11/1999 | Jacobs et al. ................. 436/10 |
| 6,146,901 A * | 11/2000 | Carver et al. ............... 436/174 |
| 6,221,668 B1 * | 4/2001 | Ryan et al. .................... 436/8 |
| 2002/0022269 A1 * | 2/2002 | Carver et al. ............... 436/372 |

FOREIGN PATENT DOCUMENTS

WO 93/17330 * 9/1993

OTHER PUBLICATIONS

Shepard, J. A., Waigh, R.D., and Gilbert, P. "Antibacterial Action of 2–Bromo–2–Nitropropane–1, 3–Diol (Bronopol)" Antimicrombial Agents and Chemotherapy, 32 p. 1693–1698 (1998).

T.W. Kuipers, et al. "Membrane Surface Antigen Expression on Neutrophils: A reappraisal of the Use of Surface Markers for Neutrophil Activation" Blood, 78p. 1105–1111 (1991).

Sandborg, R.R. and Smolen J. E., "The effects of heavy metal cations and sulfhydryl reagents on degranulation from digitonin–permeabilized neutrophils" Biochemica et Biophysica Acta, 1010 p. 330–337 (1989).

Lawrence Kass, "Staining of Granuloctic Cells by Chlorazol Black E" American Soc. Of Clinical Pathologist, 79 p.810–812 (1981).

T.Moriguchi et al., "Diamide primes neutrophils for enhanced release of superoxide anion: relationship to S–thiolationof cellular proteins" Journal of Leukocyte Biology, 60 p. 191–198 (1996).

* cited by examiner

Primary Examiner—Maureen M. Wallenhorst
(74) Attorney, Agent, or Firm—Fredrikson & Byron P.A.

(57) ABSTRACT

A control composition, and method of preparing a control composition, that includes stabilized, mammalian granulocytes having altered physical properties so that the granulocytes function as a human lymphocyte analogs when used on an automated blood cell analyzer.

22 Claims, 6 Drawing Sheets

LYM%  3.2 L
MON%  0.8 L
NEU%  94.0 H
EOS%  1.5
BAS%  0.5

LYM%  86.2 H
MON%  8.8/
NEU%  4.8/L
EOS%  0.2
BAS%  0.0

| | | |
|---|---|---|
| NEU | %N | 95.2* |
| LYM | %L | .433* |
| MONO | %M | 0.00* |
| EOS | %E | 4.39* |
| BASO | %B | 0.00* |

| | | |
|---|---|---|
| NEU | %N | 2.38 |
| LYM | %L | 96.7 |
| MONO | %M | .334 |
| EOS | %E | .557 |
| BASO | %B | 0.00 |

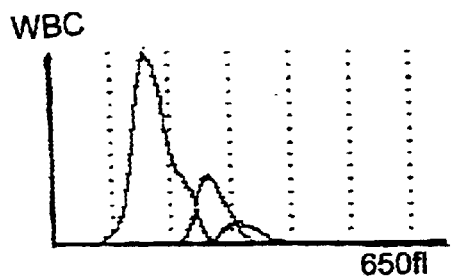
Figure 4a
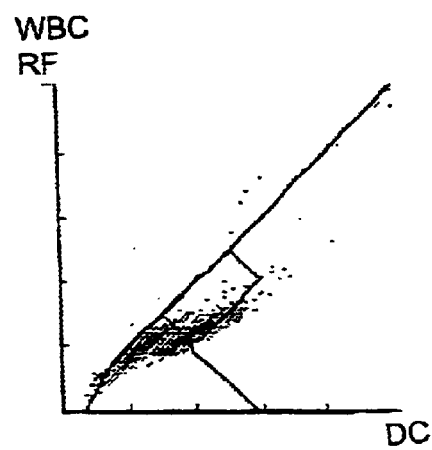
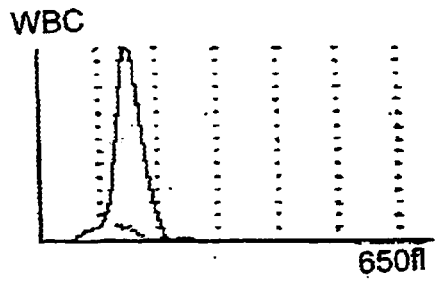
Figure 4b
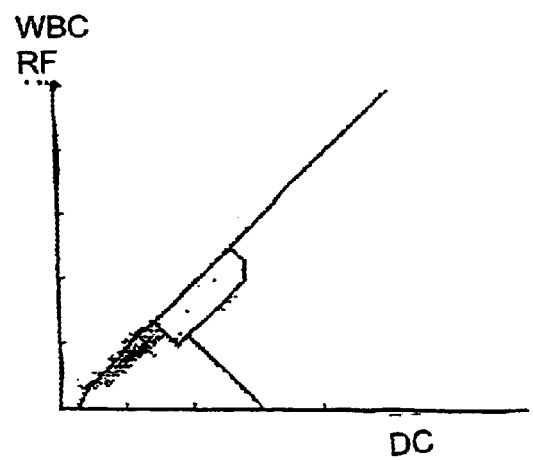

(mono, neut components added)

HEMATOLOGY CONTROL COMPOSITION INCLUDING LYMPHOCYTE ANALOGS AND METHOD FOR PREPARATION AND USE

FIELD OF THE INVENTION

The present invention relates to the field of hematology, and in particular, to assays for determining the number or presence of certain components of blood such as lymphocytes. More specifically, the invention relates to control compositions used in performing such assays, and to processes for preparing and methods of using such control compositions.

BACKGROUND OF INVENTION

To Hematology control material consisting of stabilized blood cells has long been commercially available for use in automated hematology analyzers. Methods for stabilizing cells necessarily vary depending on the reagents hematology analyzers use to dilute and treat the cells for analysis, the cell properties that are used to distinguish cell classes, and the methods of detection of these physical properties by different hematology instrumentation. In particular, classification of leukocytes may be accomplished by measurement of electrical impedance, conductivity, light scatter at various angles, selective shrinkage or resistance of cells in various diluents, or cytochemical staining. To distinguish all five major classes of leukocytes (lymphocytes, monocytes, neutrophils, eosinophils and basophils), combinations of more than one type of measurement will usually be needed.

Hematology control material may be prepared using mammalian leukocytes (generally human, porcine or bovine) or may be simulated. For example, simulation of leukocytes in control material by treatment and/or fixation of erythrocytes has been used as described in U.S. Pat. Nos. 5,512,485 and 6,146,901.

In order to supply hematology controls of varying differential white cell targets, the use of lymphocytes without contaminating leukocytes of other classes is desired, but difficult to obtain. Lymphocytes free of contaminating monocytes are particularly difficult to obtain in volumes sufficient for manufacture of hematology control materials. During leukocyte isolation, classification and stabilization, it is not unusual for monocytes to become activated and adherent, forming cell clumps that can interfere with analysis in the finished control product. Additionally, lymphocyte control materials used in instruments which use strong lytic agents (especially saponin) may require the presence of additives such as phospholipids to achieve a stable lymphocyte presentation over time, even when the lymphocytes in the control material are stabilized by fixation.

Granulocytes are more readily isolated from other leukocyte classes from whole blood using density gradients. Also, in normal mammalian blood, the number of granulocytes usually exceed the number of lymphocytes by a factor of two or more, so the pool of available granulocytes from a given quantity of blood is larger than that of lymphocytes.

It would therefore be desirable to prepare a human lymphocyte analog from a starting pool of isolated mammalian granulocytes. However, light scatter, impedance volume, conductivity of and absorbance of various dyes by granulocytes are all high compared to lymphocytes. Therefore, a hematology control prepared using granulocytes with altered physical properties such that the altered granulocytes have physical properties resembling that of human lymphocytes is desired.

SUMMARY OF THE INVENTION

The present invention provides a control composition for use in an automated blood cell analyzer comprising a predetermined concentration of stabilized mammalian granulocytes that have at least one physical property of a human lymphocyte, wherein the physical properties include, without limitation, light scatter, cytochemical dye binding, electrical impedance or other physical properties of the cell that resemble that of a lymphocyte.

The lymphocyte analogs of the invention are produced by mixing a mammalian granulocyte with a solution comprising a suitable condensation product of a nitrogen-substituted alcohol with formaldehyde, and preferably a condensation product of more than one nitrogen substituted alcohol, including without limitation, 2-bromo-2-nitropropane-1,3-diol ("Bronopol"), 5-bromo-5-nitro-1,3-dioxane ("Bronidox") or hexahydro-1,3,5-tris(2-hydroxyethyl)-s-triazine ("Triadine-3"), that allows loss of granules, granule contents, or other cytoplasmic material from the cell. The granulocyte is incubated in the presence of such solution until at least one of the physical properties of light scatter, cytochemical dye binding, electrical impedance or other physical properties of the cell measured in an automated blood cell analyzer is altered to resemble the physical properties of an isolated human lymphocyte.

Preferably, the altered granulocyte is fixed with an aldehyde fixative in a concomitant and/or subsequent step to allow sufficient stabilization of the cell for its use as a lymphocyte analog in hematological quality control material.

DESCRIPTION OF THE DRAWINGS

FIGS. 4a and 4b represent porcine granulocytes before and after treatment with Bronopol in accordance with the invention, classified by a Sysmex NE-8000 instrument. In FIG. 4a the untreated porcine granulocytes were classified as though they were a mixture of lymphocytes, monocytes and granulocytes based on their size (DC and conductivity (RF) measurements. In FIG. 4b the treated granulocytes are classified by the instrument as a single population having the DC and RF measures of lymphocytes.

DETAILED DESCRIPTION

Figure 1A:
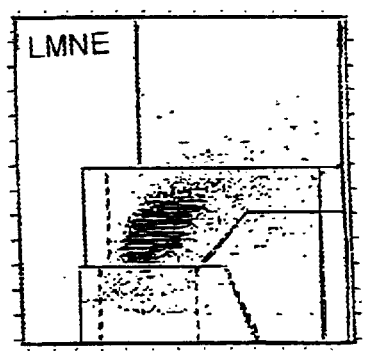
FIGS. 1a and 1b show the impedance (X-axis) and dye uptake (Y-axis) of porcine granulocytes on an ABX Pentra 60 instrument before (FIG. 1a) and after (FIG. 1b) treatment with Bronopol.

As used herein, "red cells" or "erythrocytes" will refer to peripheral blood cells of the erthyropoeitic lineage. A high concentration of hemoglobin (approximately 99% of the protein weight of erythrocytes) gives the red cells their color. Red cells can include nucleated red cells, reticulocytes, and mature red blood cells. "Red blood cells," or "RBC's," will refer to a subpopulation of red cells that comprises mature red cells only.

As used herein, "white blood cells" or "WBCs" or "leukocytes" will refer to the five types of white blood cells involved in the body's defense systems, which include, neutrophils, eosinophils, basophils, monocytes and lymphocytes.

The word "granulocyte" will refer to the white blood cells that contain intracytoplasmic granules, e.g., neutrophils, eosinophils and basophils.

The word "stabilize," or "stabilized" and inflections thereof, as used herein, will refer to cells that are provided in a form that allows the cells to be stored and used in a manner that does not unduly diminish their utility as a hematology control. Generally, stabilization involves the preparation of a suspension containing such cells in combination with one or more ingredients that are useful as preservatives. In a preferred embodiment, control compositions are provided in a form having 2-month, and preferably 3-month, or longer shelf stability when stored under refrigeration.

As used in this application the term "control" will refer to a suspension of cells or cell-like substances that is analyzed by diagnostic instruments and is intended to resemble a patient blood sample when analyzed. Such controls are provided to measure the consistency and/or accuracy of diagnostic instruments and/or methods of analysis of patient samples. Thus, such controls are manufactured to provide expected values for the various blood components. These expected values are assigned by the control manufacturer and are obtained with instruments that are more reliably maintained and calibrated than is possible in routine clinical labs. Such controls are preferably stable, so that they allow the user to establish whether the diagnostic instrument performs consistently and whether it reports the expected values. The control thus serves an important quality control function in clinical laboratories, offering assurance that the instruments and technicians are working properly and other variables are maintained in acceptable limits. Such controls can highlight when instrument service or technician training is necessary, for example.

Compositions of the present invention can be prepared from whole blood obtained from porcine, human, bovine, or other suitable mammalian source. For example, granulocytes can be prepared from whole porcine blood, or fractions thereof, according to any suitable preparative procedure.

The following is a general description of a preferred method for the harvest of porcine granulocytes. Porcine blood is collected in citrate anticoagulant with dextran added as a rouleauxing agent. Red blood cells (RBC) are allowed to settle and leukocytes (WBC) are harvested from plasma by centrifugation. Alternatively, bovine or human blood may be used, but dextran is omitted, whole blood is centrifuged and WBC are harvested from the buffy coat layer. RBC contaminating the WBC are removed by lysing with ammonium oxalate. Granulocytes are isolated with Percoll (colloidal silica sol with non dialyzable polyvinyl pyrrolidone, a trademark of Pharmacia, Sweden) by density gradient centrifugation; granulocytes will form a layer at the bottom of the container, while lymphocytes and monocytes will form a layer at the top. Granulocytes are pooled and residual Percoll is removed by diluting the cells with Coulter Isoton II (a commercial blood diluent; sodium chloride 7.93 g/l, Diasodium EDTA 0.38 g/l, Potassium chloride 0.40 g/l, Monosodium Phosphate 0.19 g/l, Sodium fluoride 0.30 g/l; sold by Coulter), alternatively, phosphate-buffered saline plus azide (PBSN) and centrifuging to harvest. In the following description, these cells are referred to as granulocytes or simply cells. One of skill in the art would understand that other methods of harvesting porcine granulocytes could also be used without departing from the present invention.

The lymphocyte analog of the invention may be prepared by contacting isolated granulocytes with a solution comprising a suitable condensation product of a nitrogen-substituted alcohol with formaldehyde, such as Bronopol, Bronidox or Triadine-3 at a concentration and for a time period sufficient so that at least one physical property of the granulocyte is altered to simulate the physical properties of a human lymphocyte in an automated hematology analyzer. Generally, this amount falls in the range of about 0.1% to 10% w/v. Preferably, the condensation product of a nitrogen-substituted alcohol with formaldehyde will be present at a concentration of about 0.5% to about 5% w/v. In a preferred embodiment the condensation product of a nitrogen-substituted alcohol with formaldehyde used is Bronopol or Bronidox at a concentration of about 0.5% w/v. In another preferred embodiment the condensation product is Triadine-3 present at a concentration of about 1.0% w/v. The time of contact will generally be between about 12 hours up to a week but most preferably about 21–24 hours.

Fixing of the altered granulocytes concomitantly with or subsequent to suspension of the cells in the treating solution including a condensation product of a nitrogen-substituted alcohol with formaldehyde, such as Bronopol, Bronidox or Triadine-3, is important to toughen the cell membranes once the cells have the physical properties of a human lymphocyte, to prevent degradation and further degranulation and to improve stability of the lymphocyte component of the final hematology control. This is accomplished by contacting the cells with a solution of an organic aldehyde, including monoaldehydes such as formaldehyde, or dialdehydes such as glutaraldehyde. Each aldehyde has different effects on parameters measured by the instruments (light scatter, impedance, conductivity, absorbance, etc.), so while other aldehydes may be used in the method of the invention, the examples and description describe the use of formaldehyde as the primary fixative and use of other aldehydes might require modifications in the procedure for fixing the cells and may not be compatible with certain reagents used with certain instruments.

The time and concentration of formaldehyde used as a fixative in the method of the invention will vary depending on the desired stability of the lymphocyte analogs and performance of the lymphocyte analog in a particular instrument. Cells not sufficiently fixed may not give the proper presentation on the instrument when measured one to several weeks after preparation of the lymphocyte analogs. One skilled in the art will be able to determine the appropriate concentration of fixative required for appropriate fixation of cells depending on the analyzer and the control composition being used. Formaldehyde has been used as a fixative for the lymphocyte analogs of the invention at concentrations in the range of about 0.25–10% w/v but is preferably about 1% w/v.

Treated granulocytes are typically held for one day (up to 7 days) at room temperature (alternatively, at 2–8° C.) with or without further mixing. Formaldehyde is then added to 1% (w/v) for an additional 24 hours (up to 7 days).

The granulocytes are washed free of fixative and a known quantity of the treated granulocytes are tested in an automated hematology analyzer to ensure that the treated granulocytes now exhibit at least one physical property of a human lymphocyte and is either stored in a plasma-like buffer without added lipids, or formulated into controls.

For some instruments, heating of the treated granulocytes prior to the inclusion of the cell in the control may improve the light scatter properties of the treated granulocytes so they more closely resemble human lymphocytes in the particular automated hematology analyzer.

A control composition of the invention will include a known quantity of the lymphocyte analogs of the invention and may also include other blood cell components, including without limitation, stabilized RBC, platelets or platelet analogs, neutrophils or neutrophil analogs, eosinophil or eosinophil analogs, monocytes or monocyte analogs and reticulocytes or reticulocyte analogs in the same buffer.

A control composition of the present invention can be used according to established laboratory hematology practice to monitor the performance of diagnostic tests. Preferred compositions are composed of stable materials that provide a means of verifying accuracy and precision of lymphocyte counting methods, as well as stabilized components necessary to serve as control material for complete blood count diagnostics.

A composition of the present invention is preferably provided in the form of an in vitro diagnostic reagent that includes the lymphocyte analog of the invention in combination with RBC's, mammalian WBC's (or analogs thereof) (other than the lymphocyte component) and platelets (or analogs thereof), all suspended in a plasma-like fluid containing suitable preservatives. A number of suitable methodologies for the preparation of RBC's, WBC's, and platelets are well know by those skilled in the art. In addition, it is well known in the art to use various analogs that mimic the physical characteristics of the different human blood cell components, but that may be easier to produce, more cost-effective, or provide greater shelf life.

Granulocytes treated in accordance with the method of the invention are suitable for use as a lymphocyte analog on ABX hematology analyzers, Abbott Cell Dyn analyzers, Sysmex analyzers such as the NE8000, and Beckman Coulter analyzers such as the STKS or the AcT 5-diff.

Normal human blood contains 500- to 1000-fold more RBC than WBC; these RBC are more sensitive to certain lytic agents than are WBC. Therefore, classification of WBC by any hematology instrument will begin by excluding RBC from the analysis, usually by selective lysis of RBC. The lytic agents will have a range of effects on the WBC, depending on the agent used, the timing of measurement after the agent is added, and the other constituents of the buffer (reagent). The most common effect is cell shrinkage, with some systems having a modest effect and others reducing the WBC to the size of its nucleus alone.

Stabilization of WBC or WBC analogs for the purpose of formulating hematology control material leaves them more resistant, but often not completely resistant, to the effects of these lytic agents. Therefore, the size of the WBC analog in the instrument/reagent system (apparent size) must match that of freshly drawn blood, where the actual size of the cells in question may differ. Because different sets of reagents are used by different instruments, the actual size of a WBC analog needed to mimic one class of WBC in freshly drawn blood will differ depending on the instrument used.

The method of measurement can also play a role. As an example, the same stabilized cell analog may appear to be a different size if impedance (DC volume) is measured than if light scatter (0° scatter) is used to determine size. The above principles are also true of other physical properties of the cell that can be measured; all are affected by the reagents and methods used to perform the measurement. Because of the variations between automated hematology analyzers, the methods of measurement of lymphocytes of several commercially available hematology analyzers and a description of reagents used with those analyzers that may affect the stability of the lymphocyte components of a hematology control are described below.

ABX Pentra and Beckman Coulter AcT-5diff (BCI AcT 5-diff) instruments.

These instruments measure WBC volume by impedance (resistivity) and absorbance of the dye Chlorazole Black. Several lytic agents are used to remove RBC from consideration, including saponin and sodium dodecyl sulfate (SDS). These powerful agents are meant to reduce the size of WBC in freshly drawn blood to that of the nucleus, plus any granules that are present. Aging of fresh blood by one or two days will increase the sensitivity of lymphocytes to the agents and make them appear smaller. Aging of stabilized lymphocyte analogs will also increase their sensitivity, but on a longer time scale of weeks or months.

Aldehyde-fixed lymphocytes respond differently over the course of one to four months to the saponin and SDS used for lysis of red cells in the differential channel. Since aldehyde-fixed lymphocytes eventually will not be recovered in the area expected for lymphocytes due to apparent decreases in resistivity during the time frame needed for optimal control material shelf life, it is difficult to manufacture a control material which recovers a stable lymphocyte percentage. In contrast, lymphocytes simulated from degranulated mammalian granulocytes in accordance with the method of this invention are recovered in the area expected for lymphocytes for a much longer period of time, allowing stable recovery of differential percentages.

A second parameter used to classify WBCs in these instruments is the uptake of dye as measured by absorbance. The dye used, Chlorazole Black, stains eosinophil granules intensely and neutrophil granules dimly. As compared to untreated granulocytes, lymphocytes are low in dye absorbance. Therefore, in order to use granulocytes to simulate lymphocytes in these instruments which result in plots of resistivity vs absorbance (due to Chlorazole Black staining), it is necessary to remove at least some of the cytoplasmic granules using the method of the invention.

Abbott Cell-Dyn instruments (3000, 3200, 3500, 3700 and 4000; all 5-part differential instruments). These instruments use scatter of polarized laser light to classify WBCs. The strategy used to classify WBCs begins with attempting to preserve light scatter characteristics of the starting cells by avoiding harsh treatment. To solve the problem of RBC interference, RBCs are induced to leak their hemoglobin, retaining intact membranes but having the same refractive index as the reagent and therefore appear invisible. Each of these instruments classify the WBCs using the same strategy, but differ in the reagents used and in the use of impedance methods to perform some or all of the cell counts (RBC, WBC, PLT).

The Cell Dyn instruments perform 5-part differentials by combining information from zero angle scatter (size), low angle scatter (complexity; related to internal membrane structure such as nucleus/cytoplasm ratio, and lobulation of nucleus), 90° scatter (from granules of granulocytes) and depolarized 90° scatter (from granules of eosinophils). Lymphocytes, in contrast to granulocytes, will be low in zero, low angle and 90° scatter.

Beckman Coulter VCS instruments (STKS, MAXM, GENS, HEMX, LH series). These instruments combine electrical impedance volume (V), electrical conductivity (C) and light scatter (S) to classify WBCs. Conductivity is dependent on the volume of the cell nucleus, and light scatter is dependent on membrane-bound organelles such as the nucleus and cytoplasmic granules. Saponin is used as a lytic agent for RBCs; it also decreases the apparent volume of WBCs. Lymphocytes are low in all three parameters (V, C and S), in contrast to granulocytes.

Sysmex NE8000. This instrument uses a lytic agent containing a polyoxyethylene alkyl ether. WBC volume is slightly decreased by this treatment, but formaldehyde, present in the lysis reagent, helps to stabilize the WBCs by fixation for the time period of the measurements. WBCs are classified by DC (impedance volume) and RF (radio frequency conductivity as determined by nuclear volume), with lymphocytes being lower in both parameters as compared to granulocytes.

Control compositions of the present invention perform well in each of the automated systems described above, as well as other known systems (e.g., ABX Diagnostics Pentra 120™, and Sysmex XE-2100™) using methodologies suggested by the manufacturers.

Without being limited, I believe that the reason that the treating solution comprising a condensation product of nitrogen-substituted alcohols with formaldehyde, such as, Bronopol, Bronidox, and Triadine-3, alters the physical properties of mammalian granulocytes is due to the ability of these compounds to act as a catalyst of sulfhydryl oxidation. Bronopol (2-bromo-2-nitro-1,3-propanediol) has been used as a preservative since the 1960s. The antimicrobial action of Bronopol, especially in the presence of oxygen, is dependent on its ability to act as a catalyst of sulfhydryl oxidation. A biproduct of this action is the production of reactive oxygen intermediates such as superoxide or peroxide. I believe the process of purifying granulocytes primes them for selective release of granules or granule contents in the presence of sulfhydryl oxidizing agents and reactive oxygen intermediates. Although Bronopol has been shown to have a fixing activity on cells treatment with Bronopol alone does not sufficiently stabilize the cells, so fixation with formaldehyde or other aldehydes following the treatment of the invention is necessary for sufficient stabilization of the lymphocyte analogs for use in a control composition.

Bronopol has been shown to have formaldehyde donor properties, however, these properties do not appear to be related to Bronopol's ability to alter the properties of mammalian granulocytes so that they have at least one physical property of a human lymphocyte. Other formaldehyde donors such as Dimethylolurea, Imidazolidinyl urea, and Diazolidinyl urea at several concentrations were used in the method of the invention but did not result in a lymphocyte analog of the invention.

Treatment of granulocytes with the treating solution of the invention prior to formaldehyde fixation allows release of a portion of cytoplasmic granules and other cell contents. The resulting analog has the physical properties of a lymphocyte, and is suitable for methods which use these properties to classify lymphocytes. In addition, the apparent volume of cells is more stably presented on instruments which use harsh combinations of lytic agents than analogs prepared from mammalian lymphocytes when control material prepared from the analogs is measured over time. No addition of phospholipid is needed to achieve a stable presentation.

The invention will be further described with reference to the following non-limiting examples.

EXAMPLES

Porcine Granulocyte Isolation

A 70% Percoll (330 mosm) solution was prepared by mixing Percoll, Isoton II and 1.5 M NaCl, osmolality of the resulting solution was approximately 330±15.

CC Dextran (Stock Solution):

The following ingredients were combined and made to 60 liters with deionized water: NaOH (24 g), citric acid (142.63 g), sodium citrate (3210 g), (3600 g) Dextran (Sigma No. D-4876, molecular weight range 150 kD to 180 kD).

CC Dextran (Diluted):

The CC Dextran solution was diluted 1:7.1 with standard phosphate buffered saline (pH 7.5+/–0.1) having (0.1%) azide as a preservative ("PBSN") (e.g., for 12 liters final, 1.69 liters of CC Dextran plus 10.31 liters of PBSN).

Example 1

Porcine granulocytes were harvested in the following manner:

1. Recovery of Porcine Blood.

Porcine blood was recovered from freshly sacrificed pigs and added to fill 20 liter carboys containing 2.5 liters of "CCD" concentrate (prepared as described above). RBCs were allowed to settle and WBCs were harvested from plasma by centrifugation in 1 Liter centrifuge bottles at 4500 rpm for 3 minutes in a Sorvall RC3-type centrifuge. Supernatants were removed by siphoning, pellets containing the WBCs were resuspended and pooled. An additional centrifugation at 4500 rpm for 3 minutes was performed to further concentrate the WBCs; supernatants were siphoned off and discarded; pellets were resuspended and pooled.

WBCs were centrifuged at 2900 rpm for 3 minutes; supernatant containing a portion of the lymphocytes was removed, and pellets were resuspended and pooled. The supernatant was aspirated.

The pellets were resuspended and combined into one centrifuge cup. The cup was filled with room temperature ammonium oxalate, mixed by inversion and allowed to sit for 10 minutes, and then centrifuged for 3 minutes at 3500 rpm. The supernatant was discarded. The cells were resuspended with ammonium oxalate and centrifuged for 3 minutes at 3500 rpm.

Residual oxalate was removed by diluting resuspended WBCs in PBSN, centrifuging for another 3 minutes at 3500 rpm, then repeating siphoning, resuspension, dilution and centrifugation. Pellets were pooled in a minimum volume of PBSN.

The entire volume of WBCs was diluted with 4 volumes of 70% Percoll (mOsm 330), mixed well and poured into centrifuge cups. The cells were diluted just before centrifuging them. The cells were centrifuged for 30 minutes at a speed of 12,000 rpm in a RC5-type Sorvall centrifuge.

After two distinct bands were formed, the bottom layer containing the granulocytes was pooled and washed by pouring no more than 300 ml in each 1-liter centrifuge cup, filling with PBSN, and centrifuging in a Sorvall RC3-type centrifuge at 3500 rpm for 4 minutes. Supernatant was discarded; pellets (granulocytes) were resuspended and pooled.

Example 2

A solution of 18 liters at osmolality of 100 mOsm/kg was prepared by mixing 5.29 liters of Isoton II (Beckman-Coulter) with 12.71 liters of deionized water. Osmolality was measured using an Advance Digi-Osmometer to verify that osmolality was between 95 and 105 mOsm/kg. Bronopol (2-bromo-2-nitropropane-1,3-diol, Aldrich cat#13, 470-8, 90 g) was dissolved in the solution for a final concentration of 0.5% (0.5 g/100 mL).

Figure 1B:
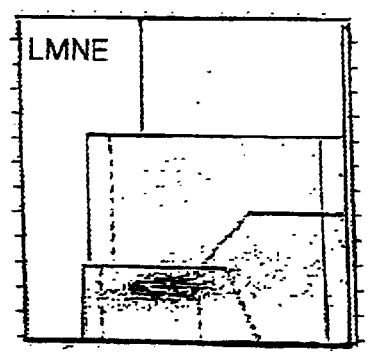

Granulocytes (2 L at $5 \times 10^8$/mL) were added to the solution for a final cell concentration lit of $5 \times 10^7$/mL and mixed by swirling. Cells were allowed to stand 24 hours at 2–8° C. without further mixing. Formaldehyde (500 ml of a 40% w/v stock) was then added for a final concentration of 1% (w/v) and cells were allowed to stand for an additional 24 hours. Cells were centrifuged in 1 liter bottles at 3000 rpm for 3 minutes in a Sorvall RC3-type centrifuge. Supernatant was decanted and cells were retained. Cells were resuspended in Isoton II and the wash process was repeated two more times. Cells were resuspended and diluted to $0.25 \times 10^9$/mL with a storage buffer. A sample was diluted 1:25 and checked on the Pentra-60 instrument to verify that cells are identified as lymphocytes and are presented within the lymphocyte area on the scatterplot. FIGS. 1a and 1b show the measurements obtained for granulocytes before and after treatment. Treatment with Bronopol lowered the dye uptake so that the treated granulocytes were identified as lymphocytes by this automated analyzer.

Example 3

A Bronopol solution was prepared by dissolving 45 g Bronopol in 9 liters of PBSN for a final concentration of 0.5% Bronopol. Granulocytes obtained as described in Example 1 (1 liter at $5 \times 10^8$/ml in PBSN) were added for a final concentration of cells at $5 \times 10^7$/ml. The mixture was rotated slowly (approximately 2 revolutions per minute) on a roller for 7 days at room temperature. Formaldehyde (250 ml of a 40% w/v stock) was then added to a final concentration of 1% (w/v) and cells were rotated for an additional 7 days. Cells were allowed to settle for 2–4 days and supernatant was decanted. PBSN was added to bring the volume to 5 liters, and cells were resuspended by swirling. Cells were poured into 1-liter centrifuge bottles and centrifuged at 3500 rpm for 15 minutes. Supernatant was decanted, cells were resuspended in PBSN and bottles were filled with PBSN. Bottles were again centrifuged at 3500 rpm for 15 minutes. Supernatant was again decanted, cells were resuspended in PBSN and bottles were filled with PBSN. Bottles were centrifuged a third time at 3500 rpm for 15 minutes. Supernatant was decanted; cells were resuspended in PBSN and diluted to approximately $10^9$/ml with PBSN (total volume 450 mL).

PBSN (2025 mL) was heated in a waterbath to 87–95° C. Cells were added to the heated PBSN (cell concentration is now $10^8$/ml) and stirred gently. Cells were stirred and sampled every 3 minutes until the peak position of the cells was <64 channels for 10 degree light scatter on a Cell Dyn 3000 analyzer (peak channel number obtained from Diagnostics mode). Cells were cooled quickly by diluting with 9 liters of PBSN that had previously been cooled to 4° C., then stored at 2–8° C. overnight. The cell suspension was filtered to remove clumps, then centrifuged in 1-liter bottles at 3500 rpm for 15 minutes to harvest the cells. Supernatants were discarded, and pellets were resuspended, pooled and diluted to approximately $10^9$/ml in a storage buffer (same one as example 1). Positional values for zero angle, low angle, 90° and 90° depolarized light scatter were verified to be within parameters for lymphocyte analogs on the CD3000 and CD4000 instruments. Cells were stored at 2–8° C. until formulation into control material for Abbott Cell Dyn analyzers. The lymphocyte analogs made by this procedure have been shown to be stable when stored at 2–8° C. for up to one year.

Figure 2A:
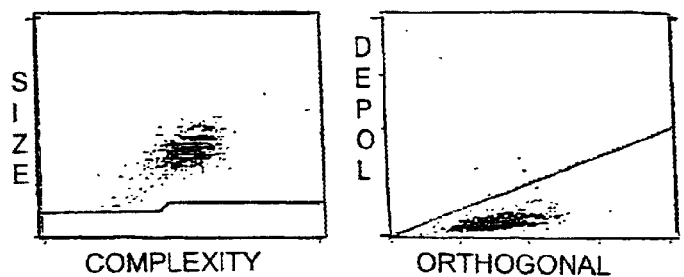
FIGS. 2a and 2b show the size (0° scatter), complexity (10° scatter) and orthogonal (90°) light scatter of granulocytes on the Abbott Cell Dyn 3000 instrument before (FIG. 2a) and after (FIG. 2b) treatment with Bronopol in accordance with the method of the invention.
Figure 2B:
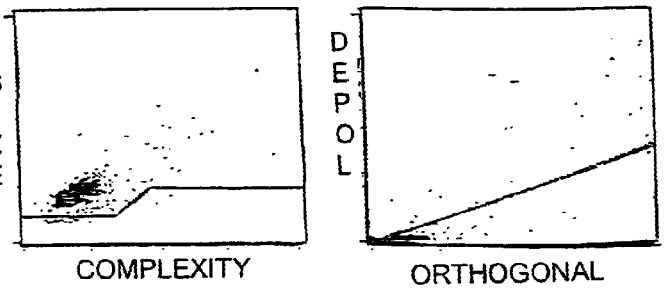
Figure 3A:
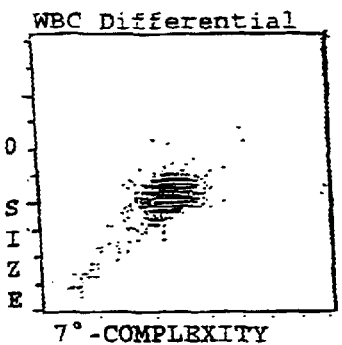
FIGS. 3a and 3b show the size (0° scatter), complexity (7° scatter) and lobularity (90°) of granulocytes on the Abbott Cell Dyn 4000 instrument before (FIG. 3a) and after (FIG. 3b) treatment with Bronopol in accordance with the method of the invention.
Figure 3A:
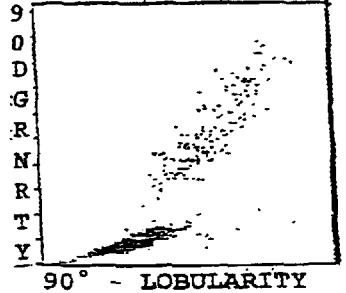
Figure 3A:
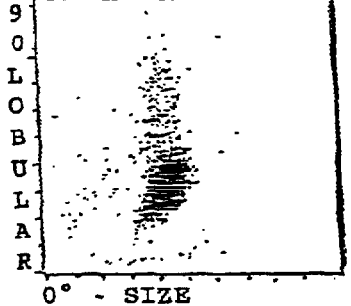
Figure 3A:
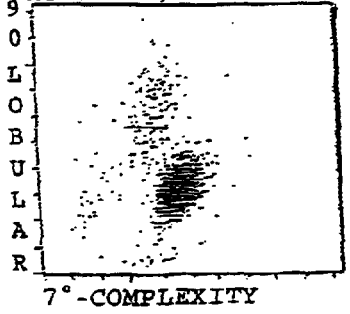
Figure 3B:
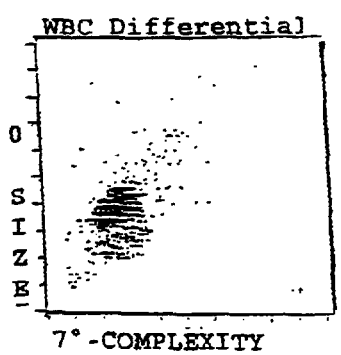
Figure 3B:
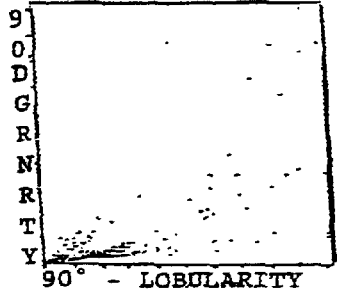
Figure 3B:
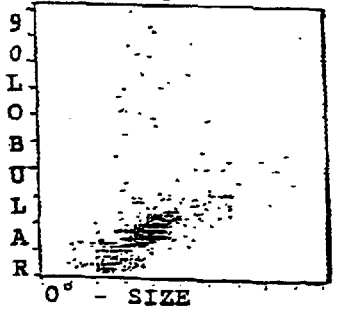
Figure 3B:
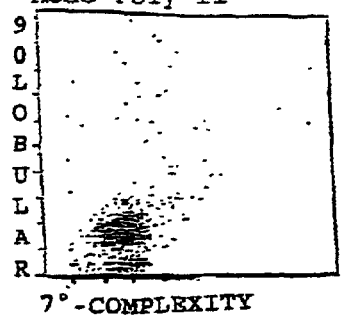

FIGS. 2a and 2b show the size (0° scatter), complexity (10° scatter) and orthogonal (90°) light scatter of granulocytes on the Abbott Cell Dyn 3000 instrument before (FIG. 2a) and after (FIG. 2b) treatment with Bronopol. FIGS. 3a and 3b show the results obtained using an Abbott Cell Dyn 4000 instrument to measure the properties of the cells before and after treatment, respectively. Treatment with Bronopol lowered light scatter of the granulocytes at all three angles and the granulocytes were identified by the instruments as lymphocytes.

Example 4

A solution of 18 liters at osmolality of 200 mOsm/kg was prepared by mixing 10.59 liters of Isoton II (Beckman-Coulter with 7.41 liters of deionized water. Osmolality was measured using an Advance Digi-Osmometer to verify that osmolality was between 195 and 205 mOsm/kg. Bronopol (2-bromo-2-nitropropane-1,3-diol, Aldrich cat#13,470-8, 90 g) was dissolved in the solution for a final concentration of 0.5% (0.5 g/100 mL).

Granulocytes (2 L at $5 \times 10^8$/mL) were added to the solution for a final cell concentration of $5 \times 10^7$/mL and mixed by swirling. Cells were allowed to stand 15 minutes. Glutaraldehyde (2.0 mL of a 25% w/v stock) was then added for a final concentration of 0.0025% (w/v) and cells were mixed by swirling and allowed to stand without further mixing overnight at room temperature. Formaldehyde (250 mL of a 40% w/v stock) was added; cells were mixed by swirling and allowed to stand for an additional 3 days, mixing daily by swirling. Cells were centrifuged in 1 liter bottles at 2500 rpm for 4 minutes in a Sorvall RC3-type centrifuge. Most of supernatant was decanted and cells were retained. Cells were resuspended in an amount of supernatant sufficient to bring the cell concentration to $1.0 \times 10^9$/mL and stored at 2–8° C. until use.

Figure 5A:
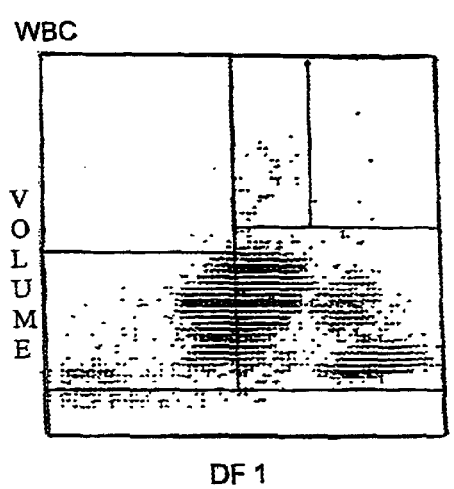
FIGS. 5a and 5b show high light scatter (DF1) of porcine granulocytes on the BCI STKS instrument before treatment with Bronopol (FIG. 5a) and that granulocytes treated with Bronopol in accordance with the invention have a reduced light scatter (FIG. 5b) and classified as lymphocytes.
Figure 5B:
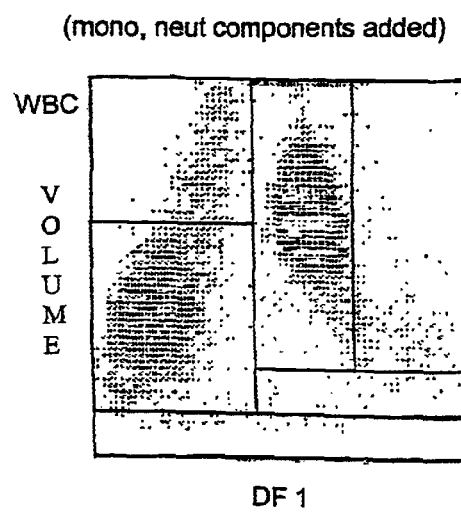

The cells were analyzed using a Beckman Coulter Inc. STKS instrument as a component of a control composition. FIGS. 5a and 5b show the light scatter (D1) of the granulocytes before and after treatment. FIG. 5b shows a fully blended control material where the lymphocyte portion represents the lymphocyte analog of the invention.

Example 5

Granulocytes were isolated and treated as described in Examples 1 and 2 and tested in a Sysmex NE-8000. Before treatment granulocytes are identified by these instruments as a mixture of granulocytes, lymphocytes and monocytes based on their size (DC) and conductivity (RF) measurements (FIG. 4a). Granulocytes treated in accordance with the method of the invention had low uniform DC and RF measurements and were identified by the instrument as a single population of lymphocytes rather than as granulocytes.

Example 6

Figure 6A:
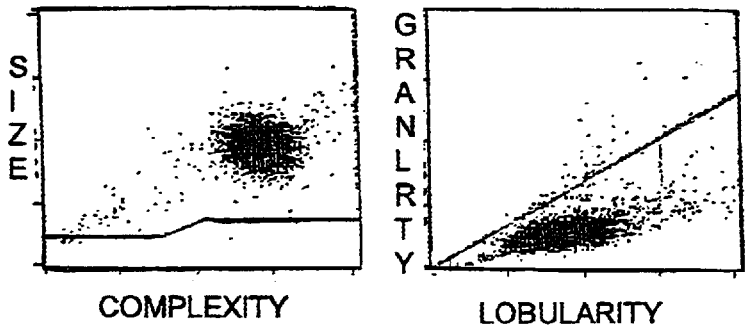
FIGS. 6a and 6b show the size (0° scatter), complexity (10° scatter) and orthogonal (90°) light scatter of bovine granulocytes on the Abbott Cell Dyn 3000 instrument before (FIG. 6a) and after (FIG. 6b) treatment with Bronopol in accordance with the method of the invention.
Figure 6B:
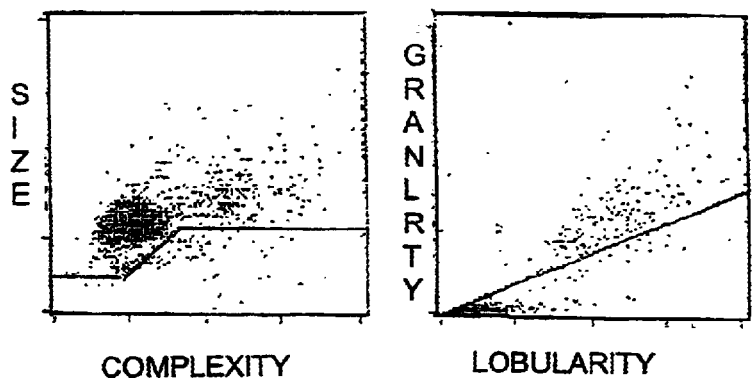

Bovine granulocytes were isolated and treated as described in Example 2 and analyzed using an Abbott Cell Dyn 3500 and 3700 instrument. FIGS. 6a and 6b show the size, complexity and orthogonal light scatter of the granulocytes before and after treatment. The results show that the lymphocyte analogs of the invention may be obtained by treating bovine granulocytes in accordance with the method of the invention as a component of a control composition.

Example 7

The lymphocyte analog prepared in Example 2 was formulated into a hematology control for the Pentra-60 instrument. To control for the maximum number of parameters and conditions seen in patient samples, hematology controls need to contain components approximating red blood cells, platelets and all five classes of WBC at varying targets over multiple levels. Red blood cells were segregated as to size (MCV), stabilized and lightly fixed, and diluted in a stabilizing plasma-like buffer at varying targets of cell count. Platelets were obtained from porcine blood, isolated from other blood cells, stabilized by aldehyde fixation, and added to the red cell matrix. In the present example WBC analogs consisting of the lymphocyte analog prepared in Example 1, neutrophil and eosinophil analogs prepared from porcine granulocytes by formaldehyde and/or glutaraldehyde fixation, and a monocyte analog prepared by fixation of bovine granulocytes, were added to the red cell matrix.

Since individual analogs are used for WBC populations, these can be blended in any proportion desired to obtain percentages of lymphocytes, neutrophils or eosinophils of 5–95%. Targets for a typical three-level hematology control are listed below:

|  | Level 1 | Level 2 | Level 3 |
| --- | --- | --- | --- |
| WBC ($\times 10^3$/ul) | 2.8 | 8.0 | 18.5 |
| Lymph. % | 50 | 30 | 12 |
| Mono % | 7 | 5 | 3 |
| Neut. % | 40 | 60 | 75 |
| Eos. % | 3 | 5 | 7 |
| MCV (fl) | 75 | 85 | 92 |
| RBC ($\times 10^6$/ul) | 2.35 | 4.65 | 5.15 |
| PLT ($\times 10^3$/ul) | 70 | 250 | 500 |

This control material is stable for a customer use period of at least 75 days. Customer use is limited by red cell aging, rather than WBC analog aging.

Several forms of invention have been shown and described, and other forms will now be apparent to those skilled in art. It will be understood that embodiments shown in drawings and described above are merely for illustrative purposes, and are not intended to limit the scope of invention defined claims which follow.

What is claimed is:

1. A method for making a lymphocyte analog for use in a hematology control product for an automated blood cell counter comprising the steps of:
   providing a mammalian granulocyte having physical properties as measured by an automated hematology analyzer at natural values; and
   suspending the granulocyte in a treating solution comprising a condensation product of a nitrogen-substituted alcohol with formaldehyde for an incubation time sufficient for at least one of the physical properties of the granulocyte to be altered to resemble the physical property of a human lymphocyte.

2. The method of claim 1 further comprising contacting the granulocyte with a fixing agent to fix the altered granulocyte to maintain the physical property of a human lymphocyte.

3. The method of claim 1 wherein the condensation product is present in the treating solution at a concentration from about 0.1% to about 10% weight/volume.

4. A method for making a lymphocyte analog for use in a hematology control product for an automated blood cell counter comprising the steps of:
   providing a mammalian granulocyte having physical properties as measured by an automated hematology analyzer at natural values; and
   suspending the granulocyte in a treating solution comprising 2-bromo-2-nitropropane-1,3-diol, 5-bromo-5-nitro-1,3-dioxane, or hexahydro-1,3,5-tris(2-hydroxyethyl)-s-triazine for an incubation time sufficient for at least one of the physical properties of the granulocyte to be altered to resemble the physical property of a human lymphocyte.

5. The method of claim 4 further comprising contacting the granulocyte with a fixing agent to fix the altered granulocyte to maintain the physical property of a human lymphocyte.

6. The method of claim 4 wherein the treating solution comprises 2-bromo-2-nitropropane-1,3-diol.

7. The method of claim 4 wherein the treating solution comprises 5-bromo-5-nitro-1,3-dioxane.

8. The method of claim 4 wherein the treating solution comprises hexahydro-1,3,5-tris(2-hydroxyethyl)-s-triazine.

9. The method of claim 4 wherein the 2-bromo-2-nitropropane-1,3-diol, 5-bromo-5-nitro-1,3-dioxane, or hexahydro-1,3,5-tris(2-hydroxyethyl)-s-triazine is present in the treating solution at a concentration from about 0.1% to about 10% weight/volume.

10. The method of claim 9 wherein the 2-bromo-2-nitropropane-1,3-diol is present at a concentration of about 0.5% weight/volume.

11. The method of claim 9 wherein the 5-bromo-5-nitro-1,3-dioxane is present at a concentration of about 0.5% weight/volume.

12. The method of claim 9 wherein the hexahydro-1,3,5-tris(2-hydroxyethyl)-s-triazine is present at a concentration of about 1.0% weight/volume.

13. A lymphocyte analog comprising a mammalian granulocyte that has been treated so that said granulocyte has at least one physical property of a human lymphocyte as measured by an automated hematology analyzer, the analog made by the process comprising:
   providing a mammalian granulocyte having physical properties as measured by an automated hematology analyzer at natural values; and
   suspending the granulocyte in a treating solution comprising a condensation product of a nitrogen-substituted alcohol with formaldehyde for an incubation time sufficient for at least one of the physical properties of the granulocyte to be altered to resemble the physical property of a human lymphocyte.

14. A lymphocyte analog comprising a mammalian granulocyte that has been treated so that said granulocyte has at least one physical property of a human lymphocyte as measured by an automated hematology analyzer, the analog made by the process comprising:
   providing a mammalian granulocyte having physical properties as measured by an automated hematology analyzer at natural values; and
   suspending the granulocyte in a treating solution comprising 2-bromo-2-nitropropane-1,3-diol, 5-bromo-5-nitro-1,3-dioxane, or hexahydro-1,3,5-tris(2-hydroxyethyl)-s-triazine for an incubation time sufficient for at least one of the physical properties of the granulocyte to be altered to resemble the physical property of a human lymphocyte.

15. A hematology control product containing a lymphocyte analog, wherein said lymphocyte analog comprises a mammalian granulocyte wherein said granulocyte possesses at least one physical property of a human lymphocyte as measured by an automated hematology analyzer, and wherein said physical property is selected from the group consisting of impedance and dye uptake, volume measured by D.C. current, high frequency (RF) conductivity, size, opacity, and light scatter at one or more angles.

16. The hematology control product of claim 15 wherein the lymphocyte analog is resistant to degradation by lytic reagents used in a hematological test procedure.

17. The hematology control product of claim 15 wherein the lymphocyte analog is the reaction product of mammalian granulocyte and a condensation product of a nitrogen-substituted alcohol with formaldehyde.

18. The hematology control product of claim 17 wherein the lymphocyte analog is resistant to degradation by lytic reagents used in a hematological test procedure.

19. The hematology control product of claim 17 wherein the condensation product is 2-bromo-2-nitropropane-1,3-diol.

20. The hematology control product of claim 17 wherein the condensation product is 5-bromo-5-nitro-1,3-dioxane.

21. The hematology control product of claim 17 wherein the condensation product is hexahydro-1,3,5-tris(2-hydroxyethyl)-s-triazine.

22. The hematology control product of claim 15 wherein the lymphocyte analog is the reaction product of mammalian granulocyte and a compound selected from the group consisting of 2-bromo-2-nitropropane-1,3-diol, 5-bromo-5-nitro-1,3-dioxane, and hexahydro-1,3,5-tris(2-hydroxyethy)-s-triazine.

* * * * *